(12) United States Patent  (10) Patent No.: US 7,892,840 B2
Chattaraj et al.  (45) Date of Patent: Feb. 22, 2011

(54) MEDIA COMPOSITIONS FOR ELUTING COMPOUNDS FROM MATRICES AND METHODS FOR MAKING AND USING THEM

(75) Inventors: Sarnath Chattaraj, Simi Valley, CA (US); Elango Minnoor, Bagalore (IN); Eugene Levin, West Hills, CA (US); Poonam S. Gulati, La Canada, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 229 days.

(21) Appl. No.: 12/346,178

(22) Filed: Dec. 30, 2008

(65) Prior Publication Data

US 2010/0162800 A1  Jul. 1, 2010

(51) Int. Cl.
G01N 33/00 (2006.01)
G01N 33/15 (2006.01)
(52) U.S. Cl. ............................................ 436/34; 436/2
(58) Field of Classification Search ................... 436/34, 436/2; 73/61.52
See application file for complete search history.

(56) References Cited

FOREIGN PATENT DOCUMENTS

WO  00/01689  1/2000
WO  2009/014755  1/2009

OTHER PUBLICATIONS

International Search Report filing date Dec. 28, 2009, International application No. PCT/US2009/069599, mailed Jul. 4, 2010.

*Primary Examiner*—In Suk Bullock
*Assistant Examiner*—Timothy G Kingan
(74) *Attorney, Agent, or Firm*—Gates & Cooper LLP

(57) ABSTRACT

Embodiments of the invention provide to apparatuses and media used in drug elution studies and methods for making and using them. One embodiment of the invention is a drug elution method that can be used for in-vitro studies of a matrix impregnated with a compound such as a drug blended polymer matrix. Such methods and materials can be used for example to assess and control the manufacturing process variability of drug eluting implantable devices such as cardiac leads.

18 Claims, 7 Drawing Sheets

MEDIA COMPOSITIONS FOR ELUTING COMPOUNDS FROM MATRICES AND METHODS FOR MAKING AND USING THEM

CROSS REFERENCE TO RELATED APPLICATIONS

This application is related to U.S. patent application Ser. No. 11/881,074, and U.S. patent application Ser. No. 12/005,952, the contents of which are incorporated by reference.

BACKGROUND OF THE INVENTION

1. Field of the Invention

The field of the invention relates to media compositions useful in elution studies (e.g. the elution of a drug from a polymeric matrix) and methods for making and using them.

2. Description of Related Art

The implantation of a medical device into a patient's body can cause the body to exhibit adverse physiological reactions ranging from infections to the formation of emboli or clots in blood vessels. One approach to address such reactions and improve the biocompatibility of such medical devices is to incorporate bioactive or pharmacological agents such as steroids, and/or antibiotics and/or anticoagulants onto a surface of these devices. Once implanted, these agents can then elute into the in vivo environment at the site of implantation and modify the physiological response.

Exemplary medical procedures that involve the implantation of medical devices include those designed to modulate cardiac physiology. For example, a variety of systems that use one or more pacing leads with electrodes such as cardiac rhythm management (CRM) systems and various techniques for implanting these lead systems in contact body tissue such as the heart, have been developed. In this context, the safety, efficacy and longevity of an electrical pulse generator of a CRM depends, in part, on the performance of the associated cardiac lead(s) used in conjunction with the pulse generator. For example, various properties of the lead and electrodes will result in a characteristic impedance and stimulation threshold. Stimulation threshold is the energy required in a stimulation pulse to depolarize, or "capture," the heart tissue. A relatively high impedance and low threshold is desired to minimize the current drawn from a pulse generator battery in delivering a stimulation pulse. Another example may be when implanting a medical device, it can result in infections in the area of infections. Such infections can be reduced by coating or otherwise combining an antibiotic with the implanted device.

One factor that can affect the stimulation threshold, particularly during the first several weeks after implantation of a lead, is the natural immunological response of the body to the lead as a foreign object. The presence of the lead activates macrophages, which attach themselves to the surface of the lead and any electrodes and form multi-nucleated giant cells. These cells, in turn, secrete various substances, such as hydrogen peroxide as well as various enzymes, in an effort to dissolve the foreign object. Such substances, while intending to dissolve the foreign object, also inflict damage to the surrounding tissue. When the surrounding tissue is the myocardium, these substance cause necrosis. These areas of necrosis, in turn, impair the electrical characteristics of the electrode-tissue interface. Consequently pacing thresholds rise. Even after the microscopic areas of tissue die the inflammatory response continues and approximately seven days after implant the multi-nucleated giant cells cause fibroblasts to begin laying down collagen to replace the necrotic myocardium. Eventually, on the order of three weeks after implant, the lead and its electrodes can be encapsulated by a thick layer of fibrotic tissue. Typically, the inflammatory response ends at this time. The fibrotic encapsulation of the lead and its electrodes, however, remains. Since the fibrotic tissue is not excitable tissue, an elevated stimulation threshold can persist due to the degraded electrical properties of the electrode-tissue interface.

One means of modulating this inflammatory response in implanted cardiac rhythm management systems has been to provide a drug near the electronic lead to mitigate the inflammatory tissue reaction described above. In particular, it has been found devices designed to elute an anti-inflammatory agent, such as a glucocorticoid steroid, minimize tissue irritation, help reduce or eliminate threshold peaking and further assist in maintaining low acute and chronic pacing thresholds. A considerable breakthrough in the development of low threshold electrode technology occurred with the invention of the steroid eluting pacing electrode of Stokes U.S. Pat. No. 4,506,680 and related Medtronic U.S. Pat. Nos. 4,577,642, and 4,606,118. Steroid, it is believed, inhibits the inflammatory response by inhibiting the activation of the macrophages. Because they do not form multi-nucleated giant cells, the subsequent release of substances to dissolve the object and which also destroy the surrounding tissue is prevented. Thus, the necrosis of any tissue by the inflammatory response is minimized as well as the formation of the fibrotic capsule. Minimizing such adverse reactions is highly desirable because it also minimizes the concomitant deterioration of the electrical characteristics of the electrode-tissue interface. The incorporation of a compound such as a steroid that elutes at the site of implantation permits pacing leads to have a source impedance substantially lower as compared to leads featuring similarly sized solid electrodes. Consequently, electronic leads which can elute compounds such as steroids also present significantly lower peak and chronic pacing thresholds than similarly sized electrodes and have therefore been adapted for patient treatment in a variety of contexts.

Implantable compositions which elute a steroid can include a drug blended with a polymeric material such as dexamethasone impregnated within a silicone polymer, a blended composition that is designed to slowly elute the steroid out of the polymer and into the surrounding tissue. Incorporating a drug such as a steroid into a device so that it wilt elute from a device upon implantation, however, increases the complexity of electronic device production as compared to non-steroid eluting devices. One potential area of difficulty in this context is the possibility of variable manufacturing processes and the potential associated effects on elution kinetics. In this context, methods and materials that allow artisans to readily examine the drug elution properties of electronic devices and other drug eluting medical devices are highly desirable. Such methods and materials can be used for example to assess manufacturing process variability of drug eluting implants and the associated quality control of such processes. Moreover, while real time in vivo elution studies may be necessary to gain a comprehensive mechanistic understanding of the modulation of the physiological reactions observed with implantation, such real time elution tests can be on the order of weeks or months. Consequently, accelerated in-vitro tests that correlate with such tests are important for manufacturing and quality control processes. For this reason, methods and materials such as media compositions that can be used to assess and control the manufacturing process variability of drug eluting implantable devices are highly desirable.

SUMMARY OF THE INVENTION

Embodiments of the invention provide media compositions useful for drug elution studies and methods for making and using them. The media and associated methods disclosed herein are designed for the elution of agents impregnated within a polymer matrix. Such methods and materials can be used, for example, to assess and control the manufacturing process variability of drug eluting implantable devices such as cardiac leads.

One embodiment of the invention is a drug elution method that can be used for in-vitro studies of a matrix impregnated with a compound such as a drug blended polymer matrix. Illustrative embodiments of the invention include methods that use a unique dissolution media to observe the elution of dexamethasone sodium phosphate from a blended polymer, a matrix that can be used for example with drug loaded pacemaker leads. This dissolution media uses a combination of constituents designed to elute compounds from within a matrix effectively and efficiently over a relatively short period of time. This dissolution media and methods for using it consequently provide an in-vitro platform for product development and quality control, particularly in the production of drug coated/impregnated medical devices.

An illustrative embodiment of the invention is a method for observing the elution of a compound from a matrix, the method comprising exposing the matrix comprising the compound to a solution comprising: 20-40% of a lower alkanol (e.g. isopropanol); and 0.2-6.0% of a matrix swelling agent; and then assaying the solution for the presence of the compound so as to observe the elution of the compound from the matrix into the solution (e.g. via a chromatographic separation technique such as HPLC). In illustrative embodiments of the invention, the matrix swelling agent comprises 0.2-1.0% diisopropyl amine; and/or dipropylamine; and/or tetramethylethylenediamine; and/or tributylamine; and/or 0.5-6% benzyl alcohol. Typically, the solution further comprises a buffer such as phosphate buffer having a pH range of pH 6 to pH 8. In one illustrative embodiment of the invention, the solution comprises 0.05M potassium phosphate buffer at pH 8; 30% isopropyl alcohol; and <1% benzyl alcohol; or <1% diisopropylamine.

The methodological embodiments of the invention can be used to study the elution of a wide variety of compounds from a wide variety of matrices. For example, the method can be used to study a plastic or other polymeric matrix having the compound impregnated, coated or embedded therein. In an illustrative embodiment, the matrix can comprise a polymer such as a silicone or polyurethane polymer and the compound can comprise a steroid, an anti-coagulant an antibiotic, or an anti-inflammatory agent. In an illustrative embodiment provided in the examples below, the matrix is a biomedical grade silicone polymer impregnated with dexamethasone sodium phosphate. Typically, the matrix and the compound are adapted for implantation in vivo, for example as part of an electronic lead of a pacemaker.

In typical embodiments of the invention, the methods are adapted to facilitate processes such as the product development and quality control of implantable drug coated medical devices. In such embodiments, the method can be practiced on a plurality of matrices produced according to a uniform manufacturing process, typically one designed to produce a plurality of matrices that elute the compound at the same rate. Optionally, the method can include the step of comparing the elution rates of two or more matrices to impregnate with a compound such as dexamethasone sodium phosphate so as to determine if the two or more matrices have the same or different elution rates.

A related embodiment of the invention is a composition of matter comprising an aqueous solution of 20-40% of a lower alkanol; and one or more matrix swelling agents comprising: 0.2-1.0% diisopropyl amine; 0.2-1.0% dipropylamine; 0.2-1.0% tetramethylethylenediamine; 0.2-1.0% tributylamine; and/or 0.5-6% benzyl alcohol. In certain embodiments of this composition, the solution comprises 0.03 to 0.05M potassium phosphate buffer having a pH range of pH 6 to pH 8; 30% isopropyl alcohol; <1% benzyl alcohol; and/or <1% diisopropylamine. In some embodiments of the invention, the composition of matter further comprises a matrix impregnated with an elutable agent comprising a steroid, an anti-coagulant an antibiotic, or an anti-inflammatory agent. Optionally for example, the matrix is a polymer matrix impregnated with dexamethasone sodium phosphate. In one illustrative embodiment of the invention, the composition further comprises a polymer matrix adapted for use as part of a cardiac lead.

A related embodiment of the invention is the use of the disclosed media compositions in an apparatus that, for example, can facilitate the practice of the above-noted methods by inhibiting the evaporation of dissolution media from the vessels in which elution is observed. In particular, the apparatus includes a cap designed to cover the vessel and inhibit dissolution media loss through evaporation (see, e.g. FIG. 7). Typically, the cap has a sample port which can optionally function as a temperature measuring port. In illustrative embodiments of the invention, a sampling cannula is introduced using this port such that the point of sampling inside the vessel can be easily adjusted. In other embodiments of the invention, the apparatus has a separate port which acts as a temperature member port. This evaporation loss cover apparatus offers easy and accurate sampling, measuring temperature and virtually no loss due to evaporation. In illustrative embodiments of the invention, the apparatus dramatically reduces evaporation to less than 1% over a one-week test period.

Embodiments of the invention also provide articles of manufacture including media system kits. In one such embodiment of the invention, a kit including the reagents disclosed herein and useful for elution studies, is provided. The kit typically comprises a container, a label and elution reagents as described above.

Other objects, features and advantages of the present invention will be apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE EMBODIMENTS

Figure 1:
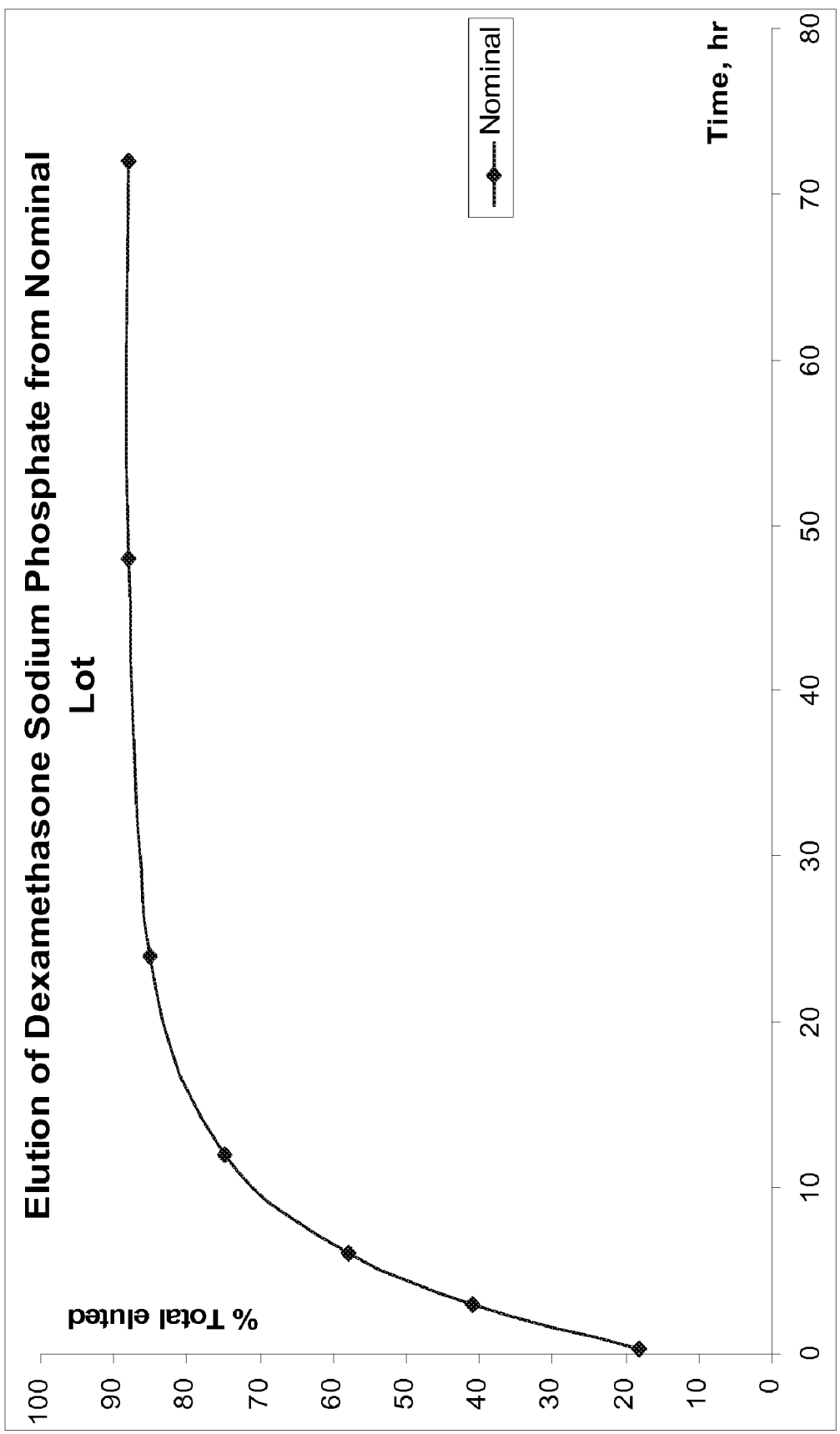
FIG. 1 shows an exemplary profile of a compound eluting from a matrix, specifically the elution of dexamethasone sodium phosphate from a drug eluting matrix used with implantable medical devices. In this study, the conditions comprised: 30% iPA+0.5% benzyl Alcohol in Phosphate Buffer, pH 8.0
Figure 2:
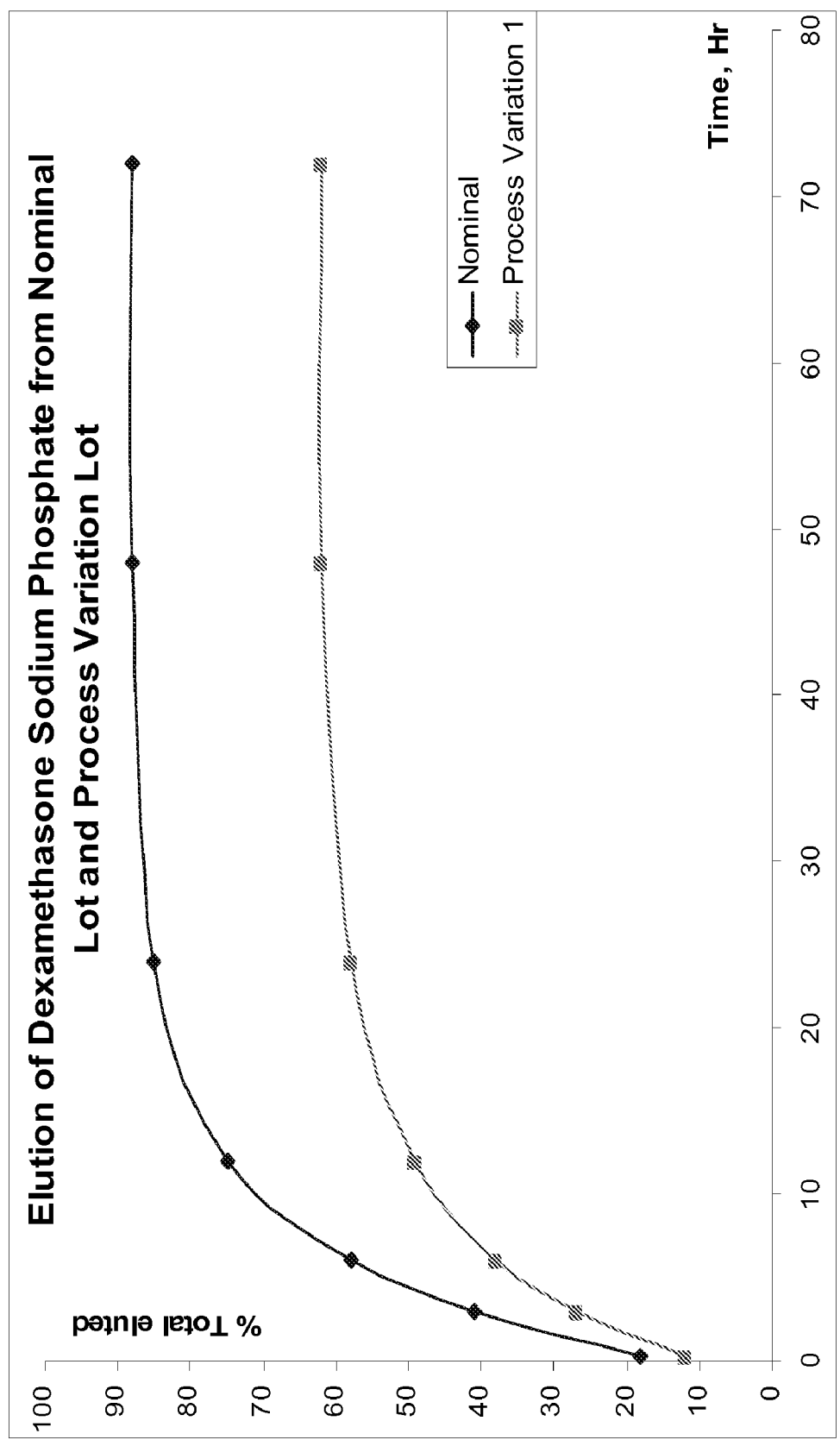
FIG. 2 shows the impact of process changes on the elution profiles of dexamethasone sodium phosphate from differing lots of drug eluting devices. In this elution discrimination study, the conditions comprised: 30% iPA+0.5% benzyl Alcohol in Phosphate Buffer, pH 8.0.
Figure 3:
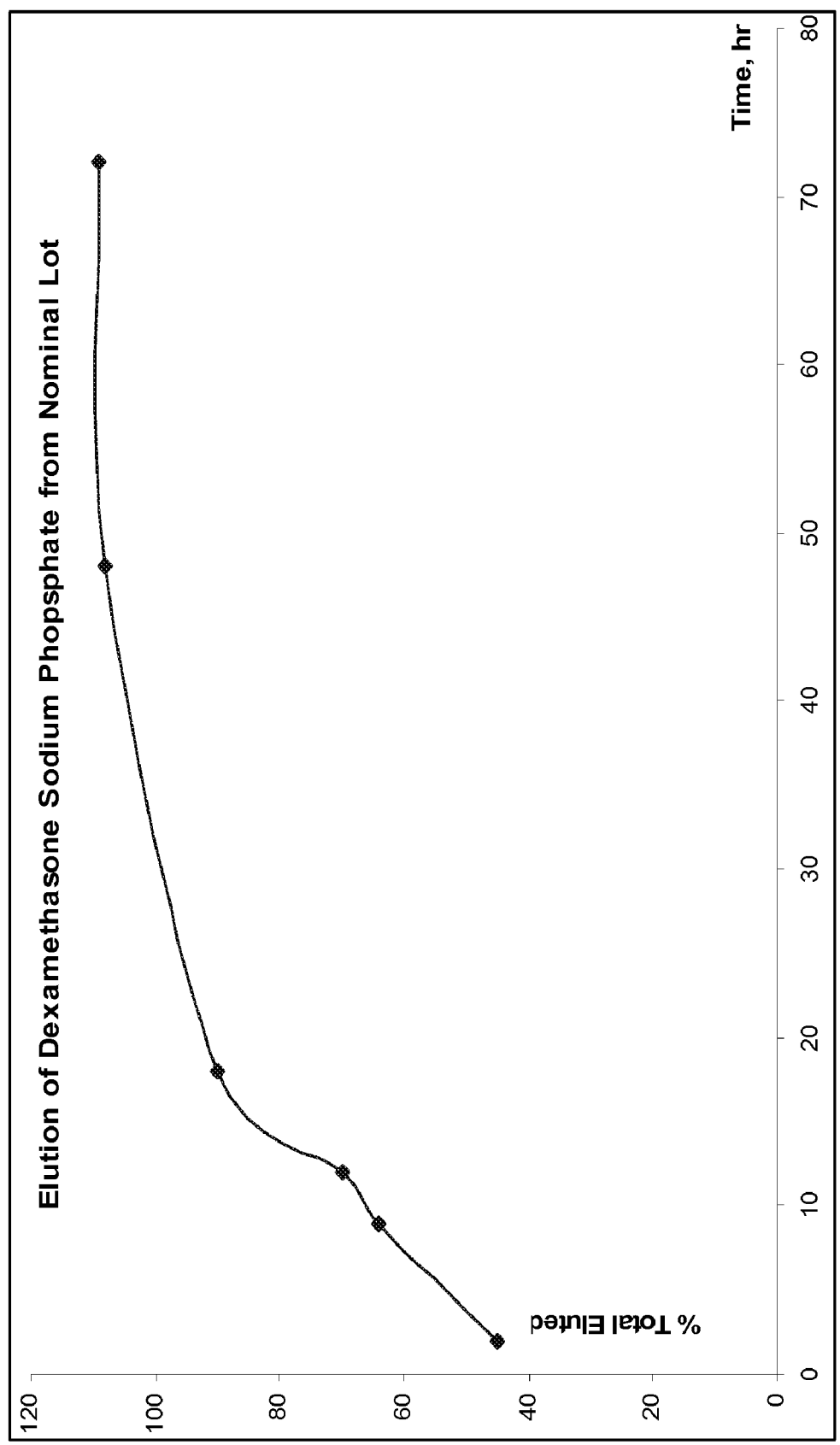
FIG. 3 shows an exemplary elution profile of dexamethasone sodium phosphate from a drug eluting device matrix. In this elution discrimination study, the conditions comprised: 30% iPA+0.5% DIPA+0.5% Benzyl Alcohol in Phosphate Buffer, pH 8.0 at 45° C.
Figure 4:
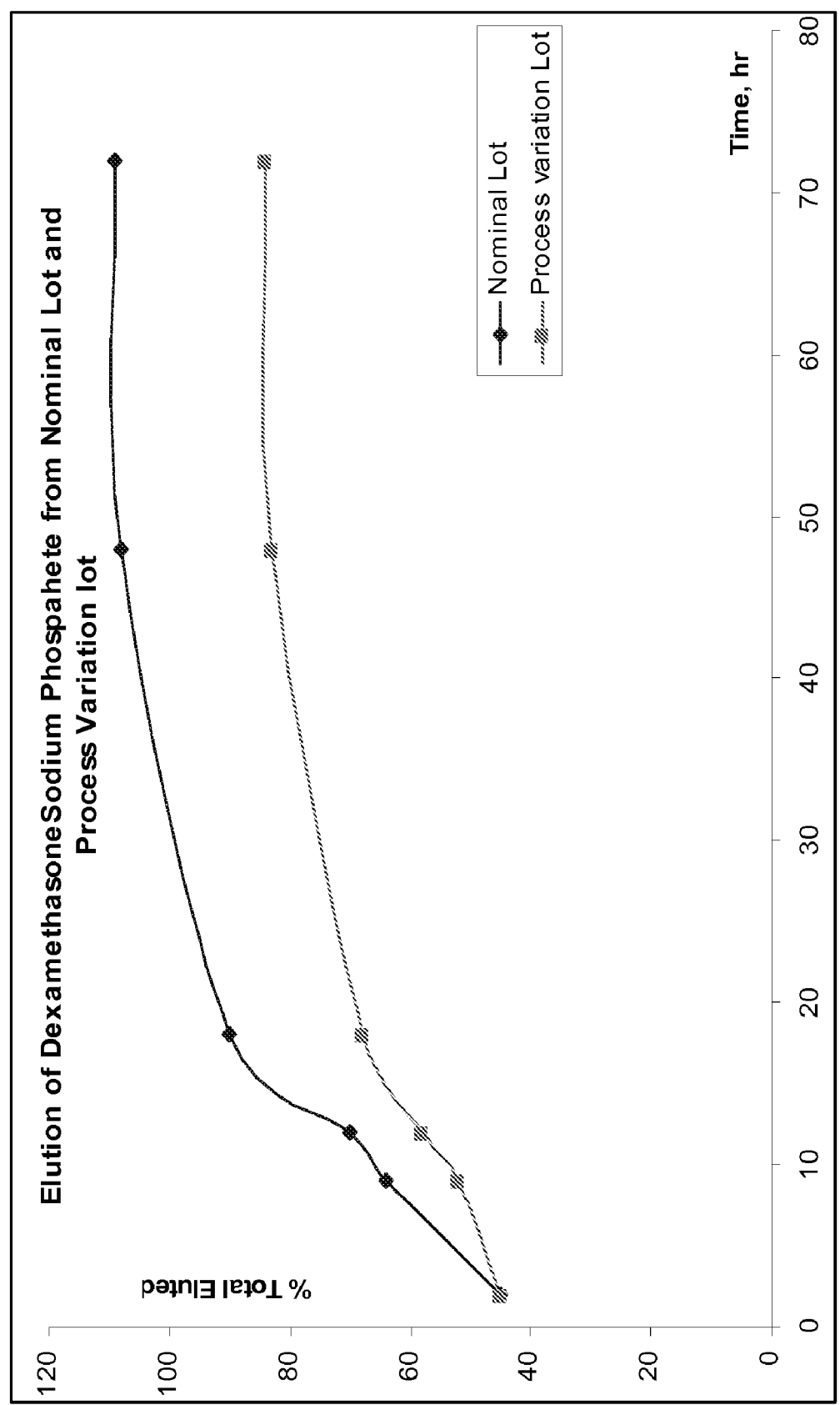
FIG. 4 shows the impact of process changes on elution profiles of dexamethasone sodium phosphate from differing lots of drug eluting devices. In this elution discrimination study, the conditions comprised: 30% iPA+0.5% DIPA+0.5% Benzyl Alcohol in Phosphate Buffer, pH 8.0 at 45° C.
Figure 5:
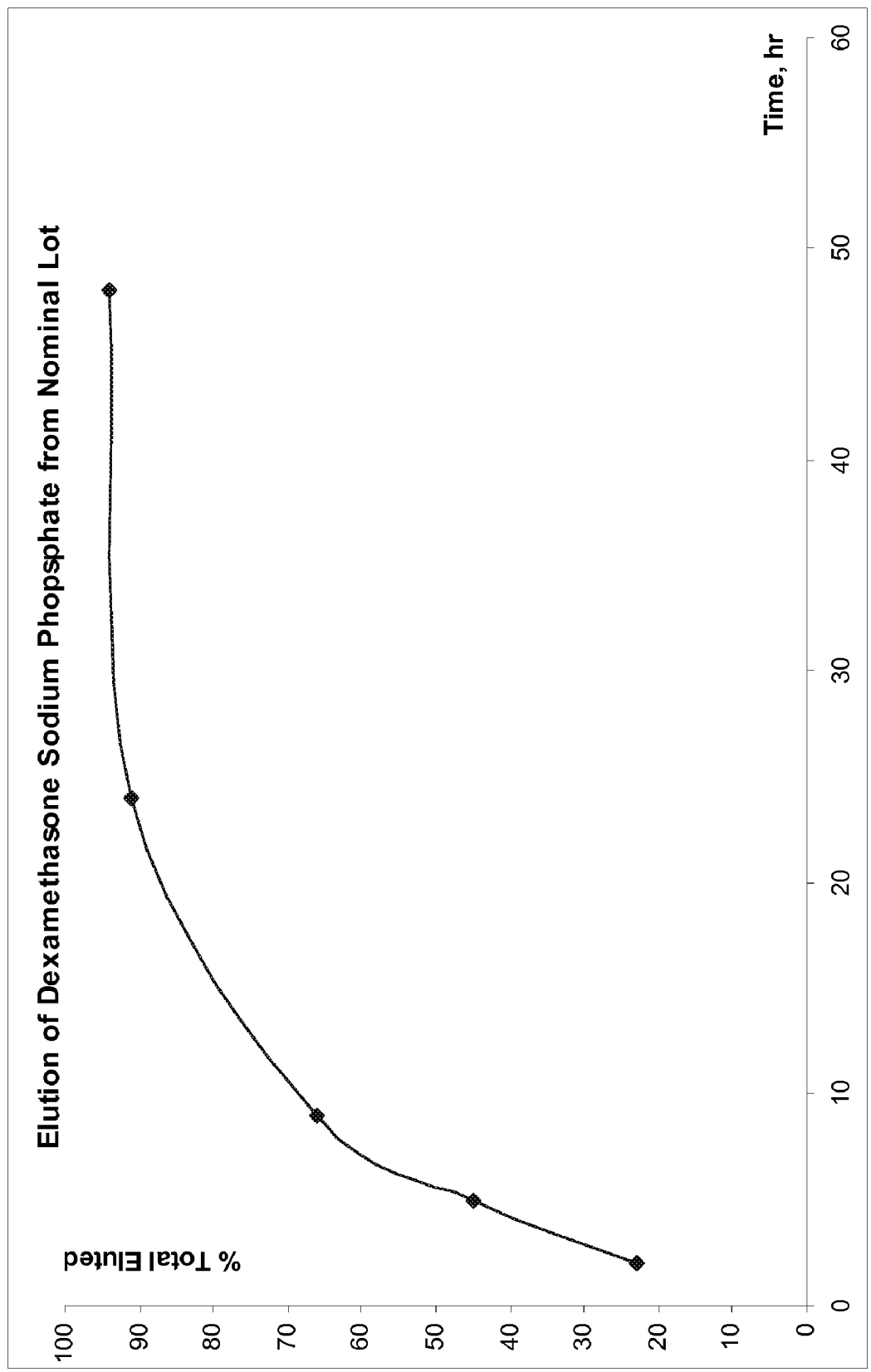
FIG. 5 shows an exemplary Elution Profile of Dexamethasone Sodium Phosphate from a drug eluting device. In this study, the conditions comprised 30% iPA+0.3% DIPA in Phosphate Buffer, pH 8.0 at 45° C.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

A. Methods and Media for Observing Drug Elution from a Matrix

The invention disclosed herein has a number of embodiments. One embodiment of the invention is a drug elution method that can be used for in-vitro studies of a matrix impregnated with a compound such as a drug blended polymer matrix. Specific embodiments of the invention include methods that use a unique media system to observe the elution of dexamethasone sodium phosphate from a drug blended polymer matrix, a matrix that is used for example with drug loaded pace maker leads. This dissolution media uses a combination of constituents designed to elute compounds from within a matrix effectively and efficiently over a relatively short period of time. This dissolution media and methods for using it consequently provide an in-vitro platform for product development and quality control, particularly in the production of drug coated medical devices.

The data disclosed in FIGS. 1-6 provides illustrative embodiments of the methods of invention that examine the elution of dexamethasone sodium phosphate from a polymeric silicone matrix. These examples provide an illustration of the power of the methodological embodiments of the invention, in particular in view of the fact that the elution of dexamethasone sodium phosphate from silicone polymer/drug coated pace maker leads is known to be minimal in conventional solvents. For example, certain elution media and methods may not be ideal for all drugs (e.g. dexamethasone sodium phosphate). For example, dexamethasone sodium phosphate is water soluble whereas typical methodologies described in the art are more suitable for water insoluble or sparingly soluble drugs. Certain media constituents (e.g. sodium lauryl sulfate (SDS) and limonene), may not work well when elute dexamethasone sodium phosphate from drug eluting devices (devices where drug is molded with polymer). Consequently, the media compositions disclosed herein were developed to overcome limitations with certain combinations of specific media compositions and specific agents as well to facilitate comprehensive studies for in-vitro drug elution from drug eluting devices. In this context, the new media compositions provide us enhanced elution properties for drugs such as dexamethasone sodium phosphate.

The media compositions disclosed herein can comprise a number of different compounds and combinations thereof. Some embodiments of the invention include an elution media containing a solvent in the form of one or more lower alkanol compounds. As used herein the term "alkanol" refers to alkanes (saturated hydrocarbons with straight or branched chain structures, with general formula CnH2n+2) having a hydroxyl group (—OH) moiety. As used herein the term "lower alkanol" refers to alkanols having 1-8 carbon atoms such as methanol, ethanol, propanol, butanol, pentanol, hexanol, heptanol, octanol or mixtures thereof. The term "lower alkanol" includes both straight chain alkanols having 1-8 carbon atoms such as 1-propanol (also known in the art as n-propanol) and 1-butanol (also known in the art as n-butanol) etc. as well as isomers such as isopropanol, isobutanol, sec-butanol, tert butanol etc. In certain embodiments of the invention, the lower alkanol is an amyl alcohol (an organic compound with the formula C5H12O) such as 1-pentanol, 3-methyl-1-butanol, 2-methyl-1-butanol, 2,2-dimethyl-1-propanol, 3-pentanol, 2-pentanol, 3-methyl-2-butanol or 2-methyl-2-butanol. In some embodiments of the invention, the lower alkanol is ethanol or n-butanol. In one specific embodiment of the invention, the elution media comprises the lower alkanol isopropyl alcohol (also called 2-propanol, iso-propanol and isopropyl alcohol). Isopropyl alcohol (IUPAC name: propan-2-ol, CAS number 67-63-0) is an organic compound having the formula C3H8 O and a molecular weight of 60.10 g/mol.

Embodiments of the media compositions typically comprise a matrix swelling agent. The term "matrix swelling agent" is used according to its art accepted meaning and refers to a solvent having properties that allow a matrix to swell so as to increase the porosity of the matrix and achieve a desired increase in elution kinetics. A wide variety of matrix swelling agents are known in the art. Such swelling agents include for example organic acids, organic alkylated amines such as methyl/ethyl/butyl and propylamines and organic alcohols. Specific swelling agents know in the art include for example trifluoroacetic acid (TFA) and hydrogen fluoride (HF), dichloromethane (DCM), acetonitrile (ACN), benzyl alcohol, limonene and isopropanol (IP). A number of the illustrative matrix swelling agents described below are those selected for their ability increase the porosity of matrices commonly disposed on implantable medical devices such as polymeric silicones and polyurethanes. In typical methodological embodiments of the invention, this type of polymeric material is contacted with the matrix swelling agent under condition and for a sufficient period of time to promote swelling of the matrix thereby causing diffusion/migration of the compound from the matrix into the surrounding media.

Some embodiments of the invention include an elution media containing an agent selected for its ability to swell a polymeric matrix used with implantable medical devices so as to facilitate agent elution from the polymeric matrix. In certain embodiments of the invention, the elution media comprises diisopropyl amine as such a swelling agent. Diisopropylamine (IUPAC name: N-isopropylpropan-2-amine, CAS number 108-18-9) is a secondary amine with the chemical formula (CH3)2HC—NH—CH(CH3)2 and a molecular weight of 101.19 g/mol. DIPA is for example used in media compositions designed for embodiments of the invention directed to silicon matrices because it is observed to be one of the compounds that swells silicone to the greatest extend. In certain embodiments of the invention, the elution media comprises dipropylamine (also called N,N-Dipropylamine; N-Propyl-1-propanamine; Di-n-propylamine, CAS number 142-84-7) as a swelling agent. In certain embodiments of the invention, the elution media comprises tetramethylethylenediamine (also called N,N,N',N'-Tetramethylethylenediamine, CAS number 110-18-9) as a swelling agent. In certain embodiments of the invention, the elution media comprises tributylamine (also called N,N-Dibutyl-1-butanamine, CAS number 102-82-9) as a swelling agent.

In certain embodiments of the invention, the elution media comprises additional compounds such as benzyl alcohol. Benzyl alcohol (IUPAC name: Phenylmethanol, CAS number 100-51-6) is an organic compound having the formula C6H5CH2OH and a molecular weight of 108.14 g/mol. Benzyl alcohol is partially soluble in water (4 g/100 mL) and completely miscible in alcohols and ether. In certain embodiments of the invention an agent such as Benzyl Alcohol can exhibit multiple functionalities in an elution methodology and can for example act as a swelling agent as well as a preservative for dexamethasone sodium phosphate.

The media compositions disclosed herein can comprise a number of different buffers and combinations thereof. In certain embodiments of the invention, the elution media comprises a potassium (or sodium) phosphate buffer. Such buffers are well known in the art and readily prepared by artisans in this technology. Typically for example, one starts with powder stocks of the commercially available compounds: K2HPO4 and KH2PO4. The powder stocks are used to prepare two solutions. Molarity depends on the molarity of the final solution: if one is preparing a solution of 0.05 M phosphate buffer, each of the two K2HPO4 and KH2PO4 solutions can be made with molarity of 0.05M. The desired pH can then be obtained by mixing the two solutions in the appropriate way (the K2HPO4 solution pH is more than 8, while the KH2PO4 solution pH is about 6.8). In one illustrative elution buffer used with embodiments of the invention is made according to the following recipe. A 0.05 M Potassium Phosphate Monobasic Solution is first prepared by weighing 6.8 grams of Potassium Phosphate Monobasic into a 1000 ml volumetric flask, diluting it with process water to volume, and mixing. A 0.05 M Potassium Phosphate Dibasic Solution is then prepared by weighing 8.7 grams of Potassium Phosphate Dibasic into a 1000 ml volumetric flask, diluting it with process water to volume, and mixing. 0.05M Phosphate Buffer, pH 8.0 is then prepared by carefully titrating the Potassium Phosphate Monobasic with the Potassium Phosphate Dibasic solution until pH 8.0±0.1 is reached when measured at 20-25° C. Other buffer systems can be readily adapted to embodiments of the disclosed media compositions using well known protocols (see, e.g. "Buffer Solutions: The Basics" (Basics (Oxford England)) by R. J. Beynon and J. S. Easterby (1996) and "pH and Buffer Theory: A New Approach" (Wiley Series in Solution Chemistry, V.1) by H. Rilbe (1996)). In this context, the skilled artisan understands that a wide variety of buffer systems are well known in the art (e.g. PBS, TRIS, HEPES, MOPS, PIPES, MES, MOPSO, TAPSO, POPSO, DIPSO, HEPPSO, CAPSO, AMPSO etc.). In some embodiments of the invention, one can use TRIS with acetate, phosphate or citrate buffers at the appropriate pH.

Embodiments of the disclosed media compositions can be used to elute a variety of compounds from a variety of matrices. Illustrative embodiments include drug elution methods that can be used for in-vitro studies of drug eluting devices (drug blended polymer matrix). For example, an embodiment of the method was used with Dexamethasone sodium phosphate (DSP) impregnated within a silicone blended matrix. Details of the method including the contents of the dissolution media for determining the DSP from the drug blended polymer matrix, with special emphasis to drug loaded pace maker leads is disclosed herein. Such embodiments of the dissolution media use a unique chemical mixture that is capable of eluting the drug effectively and efficiently, providing an in-vitro platform for product development and quality control. The dissolution media is composed of varying amounts of isopropyl alcohol (IPA), benzyl alcohol, and Diisopropyl amine (DIPA). In these embodiments, the concentration of isopropyl alcohol was about 30% while the concentration of benzyl alcohol and diisopropyl amine was maintained below 1% each. In a first medium embodiment, IPA in combination with DIPA was surprisingly effective for use with MCRDs made of silicone material. In another medium embodiment, Benzyl alcohol in combination with IPA was surprisingly effective for use with devices made of polyurethane. In addition, the combination of IPA, benzyl alcohol and DIPA was surprisingly effective for use with leads that were made of silicone. Such media composition embodiments therefore overcome difficulties with elution studies relating to both the individual elution profiles of different matrix materials (e.g. silicone as compared to polyurethane) as well as the need to be able to assess the elution profile of an agent from a matrix in a relatively short time period (e.g. so as to allow a comprehensive elution study in 72 hours of an agent that is designed to elute over at least 10, 20, 30, 60 or 90 days in vivo).

The methods and compositions of the invention can be used in a variety of contexts and are particularly well suited for studies of materials variations that can occur for example within a batch of processed materials and/or between batches of processed material. The terms "batch" and "lot" are used according to their art accepted meaning and refers to a specific quantity of a drug or other material produced (typically according to a single manufacturing order during the same cycle of manufacture) and intended to have uniform character and quality, within specified limits. As shown in the examples below, this media system is proven to be discriminatory for detecting process variations in manufacturing processes.

While the methodological embodiments of the invention can be used to assess the elution of a wide variety of compounds from a wide variety of matrices, these methods of the invention are particularly useful in the context of the manufacture of drug eluting implantable medical devices. For example, the safety and efficacy of drug coated pace maker leads are readily evaluated using the unique dissolution methods and materials disclosed herein. In contrast, due to the extended release nature of the product and also due to the free solubility of dexamethasone sodium phosphate, the elution of the drug is observed to be minimal in conventional media systems, for example a media that utilizes just a surfactant.

The invention disclosed herein has a number of embodiments. One illustrative embodiment of the invention is a method for observing the elution of a compound from a matrix, the method comprising combining the matrix comprising the compound to a solution comprising: 20-40% of a lower alkanol (e.g. isopropanol); and 0.2-6.0% of a matrix swelling agent; and then assaying the solution for the presence of the compound so as to observe the elution of the compound from the matrix into the solution (e.g. via a chromatographic separation technique such as HPLC). In illustrative embodiments of the invention, the matrix swelling agent comprises 0.2-1.0% diisopropyl amine; dipropylamine; tetramethylethylenediamine; or tributylamine; and/or 0.5-6% benzyl alcohol. Typically, the solution further comprises a buffer such as phosphate buffer having a pH range of pH 6 to pH 8. In one illustrative embodiment of the invention, the solution comprises 0.05M potassium phosphate buffer at pH 8; 30% isopropyl alcohol; and <1% benzyl alcohol; or <1% diisopropylamine. Typically, the method comprises combining the matrix comprising the compound with the solution and then observing the elution of the compound from the matrix into the solution over time.

One typical embodiment of the invention is a method for observing the elution of a compound from a matrix comprising the compound into a solution. In typical embodiments of this method, the solution comprises 0.03 to 0.05M potassium phosphate buffer having a pH range of pH 6 to pH 8; 20-40% isopropyl alcohol; 0.5-6% benzyl alcohol; and/or 0.2-1% diisopropylamine. In one embodiment of this method, the solution comprises 0.03 to 0.05M potassium phosphate buffer having a pH of 6-8; 30% isopropyl alcohol; and <1% benzyl alcohol; and/or <1% diisopropylamine.

Embodiments of the invention comprise a unique constellation of components that is shown to elute dexamethasone sodium phosphate molded with a polymer under time and conditions that allow the method to be used in the evaluation of manufacturing processes, for example to confirm that samples from various batches have elution properties within a set of characteristic parameters. Some embodiments of the invention may include a 20-40% isopropyl alcohol solution having other components known in the art and used in elution studies, for example phosphate buffer having a pH range of pH 6 to pH 8 and/or anionic (e.g. sodium dodecyl sulfate), cationic (e.g. Cetyl trimethyl ammonium bromide—CTAB) and non-ionic (e.g. Solutol HS 15-poly-oxyethylene esters of 12-hydroxystearic acid, Tween 80) surfactants.

Embodiments of the method can be manipulated by modifying the conditions under which elution is observed, for example, by observing elution at a specific solution temperature or temperature range, e.g. at 25, 30, 37, 40, 41, 42, 43, 44 or 45 degrees centigrade or between 25 and 45 degrees centigrade. In addition, typical embodiments of the invention include the steps of agitating the solution with a stirring device, shaker or use a flow through device like USP apparatus 4. Typically, the volume of the solution used in such methods is between 50 and 150 milliliters (e.g. 50, 75, 100, or 125 milliliters). In some embodiments of the invention, the specific formulation of the media is selected for specific elution characteristics, for example, an ability to elute at least 50% (or 60% or 70% or 80%) of dexamethasone sodium phosphate impregnated within a polymeric silicone matrix in 72 hours at 37, 38, 39, 40, 41, 42, 43, 44, or 45 degrees centigrade.

In describing this invention, the term "matrix" simply means any material in which a compound can be coated on to, and/or combined with and/or embedded within and/or enclosed within. Similarly, the "matrix comprising the compound" is a material having a compound such as a steroid and/or anticoagulant and/or antibiotic or the like loaded and/or coated on it and/or embedded within it and/or enclosed within it. Such methods for observing the elution of a compound from a matrix by exposing the compound to a solution and then observing the presence of the compound in the solution over a period of time can be used to observe a wide variety of matrices and compounds. Such assays can be used to determine what percentage of a compound (e.g. 0% up to 100% of a drug loaded compound) is eluted under specific conditions (e.g. concentration of various components of the media and/or pH and/or temperature etc.) over various periods of time (e.g. 1 minute, 1 hour, 1 day or 1 week etc.).

Elution of a compound from a wide variety of matrices are known in the art can be observed in the methodological embodiments of the invention. In typical embodiments of the invention, the matrix is an implantable polymer matrix. Typically, polymer matrices observed in the methods of the invention are biocompatible and designed to minimize irritation at the site of implantation. In certain embodiments of the invention, the polymer may be either a biostable or a bioabsorbable polymer depending on the desired rate of release or the desired degree of polymer stability. Biostable polymers such as polyurethanes, silicones, and polyesters are used in certain embodiments of the invention. In the examples provided below, the illustrative matrix used to demonstrate embodiments of the invention is a biomedical silicone polymer impregnated with Dexamethasone sodium phosphate. Other polymers can also be used in certain embodiments of the invention such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose. Bioabsorbable polymers include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly (iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. In other embodiments of the invention, the matrix can be a metal such as one of the metals typically used in portions of implantable medical devices that are exposed to living tissue.

A wide variety of compounds can be coated on to, and/or combined with and/or embedded within and/or enclosed within a matrix to produce a matrix comprising the compound. For example, compounds examined or assayed by an embodiment of the present invention can be virtually any compound which possesses desirable therapeutic characteristics for implantation. In some embodiments, the compound is a glucocorticoid such as dexamethasone, dexamethasone sodium phosphate, dexamethasone acetate or another dexamethasone derivative as well as related molecules such as beclamethasone or betamethasone. In one illustrative embodiment of the invention, the matrix comprising the compound is a matrix having the compound blended therein, for example a 60-80% silicone polymer (e.g. a biomedical grade silicone polymer) impregnated with a compound such as dexamethasone sodium phosphate.

As noted above, wide range of matrix and compound materials known in the art can be studied in the methodological embodiments of the invention including metal, plastic and other polymeric matrices as well as compounds such as a steroid, an anti-coagulant an antibiotic, or an anti-inflammatory agent, for example heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine, a glycoprotein IIb/IIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodelling inhibitor; deoxyribonucleic acid, an antisense nucleotide or another agent for molecular genetic intervention; methotrexate or another antimetabolite or antiproliferative agent; an anti-cancer chemotherapeutic agent; dexamethasone, dexamethasone sodium phosphate, dexamethasone acetate, belcomethasone (e.g. belcomethasone dipropionate) or another dexamethasone analog or derivative, or another anti-inflammatory steroid or non-steroidal antiinflammatory agent; cyclosporin or another immunosuppressive agent; trapidal (a PDGF antagonist), angiopeptin (a growth hormone antagonist), an anti-growth factor antibody, or another growth factor antagonist; dopamine, bromocriptine mesylate, pergolide mesylate or another dopamine agonist radiotherapeutic agents; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxamine, a 21-aminosteroid (lasaroid) or another free radical scavenger, iron chelator or antioxidant of any of the foregoing; or a mixture of any of these. The ratio of compound to the matrix (e.g. a therapeutic substance such as dexamethasone to a silicon polymer) will vary according to how the compound and matrix are used. A wide ratio of compound to matrix ratios can therefore be appropriate and can range from about 10:1 to about 1:100.

As discussed above, the methodological embodiments of the invention can be used to study matrices impregnated and/or coated with compounds that are used or implanted in vivo including those used with pacemaker leads (e.g. in rings and tips for leads), stents, sensors, medication delivery pumps, catheters, balloons, wire guides, cannulae, and the like) and in vivo and ex vivo antimicrobial coatings and similar coatings and covers. In addition, the methods and materials of the various embodiments of the invention can be used to assay matrices and compounds that are not implanted, such as a matrix comprising a compound that is used in industrial application, for example, compound impregnated matrices used in fermentation processes. Embodiments of the invention are adapted for observing matrices produced in batches according to one or more carefully controlled manufacturing processes (e.g. as part of a manufacturing process controlled in accordance with FDA guidelines). An exemplary embodiment of the invention involves performing the method on a plurality of matrices produced according to a uniform manufacturing process. A related embodiment of the invention involves performing the method on a plurality of such matrices made by a process designed to produce a plurality of matrices that elute the compound at the same rate. Another embodiment of this method involves further analytical steps, for example comparing the elution rates of two or more of plurality of matrices to determine if the two or more matrices have the same or different elution rates.

A wide variety of methods known in the art can be used to observe the compound in the solution including chromatographic methods such as HPLC and the like as well as immunoassays such as enzyme linked immunoadsorbent assays and the like. In view of the level of skill in this art, artisans can use any one or a wide variety of detection techniques and/or any separation technique followed by detection. Illustrative but non-limiting examples of such techniques include capillary electrophoresis, HPLC-UV; HPLC-MS (MS=Mass Spectroscopy); UPLC-UV (UPLC=Ultra performance LC) and; if for example the drug is volatile, techniques such as gas chromatography-flame ionization detection (GC/FID) in GC/FID, the FID or flame ionization detector detects analytes by measuring an electrical current generated by electrons from burning carbon particles in the sample. See, e.g. HPLC Method Development for Pharmaceuticals, Volume 8 (Separation Science and Technology), 2007 Academic Press, $1^{st}$ ed., Ahuja and Rasmussen (Editors); and Handbook of HPLC (Chromatographic Science), 1998, Marcel Dekker $1^{st}$ ed. Katz et al eds.

Related embodiments of the invention include compositions of matter: (1) made for; or (2) produced by the methods disclosed above, for example, a composition of matter comprising an aqueous solution of 20-40% of a lower alkanol; and one or more matrix swelling agents comprising: 0.2-1.0% diisopropyl amine; 0.2-1.0% dipropylamine; 0.2-1.0% tetramethylethylenediamine; 0.2-1.0% tributylamine; or 0.5-6% benzyl alcohol. In certain embodiments of this composition, the solution comprises 0.03 to 0.05M potassium phosphate buffer having a pH range of pH 6 to pH 8; 30% isopropyl alcohol; <1% benzyl alcohol; and/or <1% diisopropylamine. In some embodiments of the invention, the composition of matter further comprises a matrix impregnated with an elutable agent comprising a steroid, an anti-coagulant an antibiotic, or an anti-inflammatory agent. Optionally for example, the matrix is a polymer matrix impregnated with dexamethasone sodium phosphate. In one illustrative embodiment of the invention, the composition further comprises a polymer matrix adapted for use as part of a cardiac lead.

As noted above, certain specific embodiments of this composition of matter further comprise a polymer matrix impregnated with a steroid or anti-coagulant. In this context, artisans will understand that a wide variety permutations of such solutions can be readily made with minimal effort, for example 0.03 to 0.05M potassium phosphate buffer having a pH range of 6 to 8 (as well as half and quarter values of these numbers such as pH 6.5 and 6.25 etc.), in combination with a swelling agent at a concentration of 0.1%, 0.25%, 0.5%, 0.75%, 1%, 2%, 3%, 4%, 5%, or 6% (as well as half and quarter values of these numbers such as 1.5% and 1.25% etc.), in combination with a lower alkanol at a concentration of 20%, 25%, 30%, 35%, or 40% (as well as half and quarter values of these numbers such as 22.5% and 21.25% etc.). Certain specific embodiments of this composition of matter further comprise a polymer matrix impregnated with an agent designed to facilitate in vivo implantation of an apparatus such as a steroid or anti-coagulant.

In some embodiments of the invention, the composition of matter further comprises a matrix impregnated with an elutable agent comprising a steroid, an anti-coagulant an antibiotic, or an anti-inflammatory agent. Optionally for example, the matrix is a polymer matrix impregnated with dexamethasone sodium phosphate. In one illustrative embodiment of the invention, the composition of matter further comprises a polymer matrix is adapted for use as part of a cardiac lead.

All numbers recited in the specification and associated claims (e.g. pH 6 to pH 8; 0.1-6% matrix swelling agent, and 20-40% lower alkanol) are understood to be modified by the term "about".

B. Apparatus for Inhibiting Evaporation from a Vessel

A variety of vessels can be used in embodiments of the elution methods disclosed herein, for example the well known USP apparatuses discussed below. In this context, one embodiment of the invention is an apparatus that is used, for example, to facilitate the practice of the above-noted methods by inhibiting the evaporation of an elution media from the vessels in which elution is observed. In particular, the accuracy of quantification of a drug such as dexamethasone sodium phosphate in dissolution/elution tests greatly depends upon maintaining the volume of the elution media. Evaporation is a significant issue due to the reduced amount of elution media used for the drug coated devices. If the volume decreases due to evaporation, it will lead to over estimation of the drug content. This is a significant issue in extended release products which are tested for a longer period of time.

Typically, the apparatus includes a cap designed to cover the vessel and inhibit elution media loss through evaporation. This evaporation loss cap apparatus offers easy and accurate sampling, measuring temperature and virtually no loss due to evaporation. Embodiments of the invention are useful for example in the development, production and release of drug eluting products. For example, when a product will not be approved by regulatory bodies without an appropriate elution method for studying possible process variability, the method can significantly depend upon the integrity of the cover of the vessel. In illustrative embodiments of the invention provided in the examples below, the apparatus reduces evaporation to less than 1% over a period of one week. This embodiment of the invention therefore demonstrates how dramatically the invention can reduce the evaporation of media from a dissolution vessel.

Figure 7:
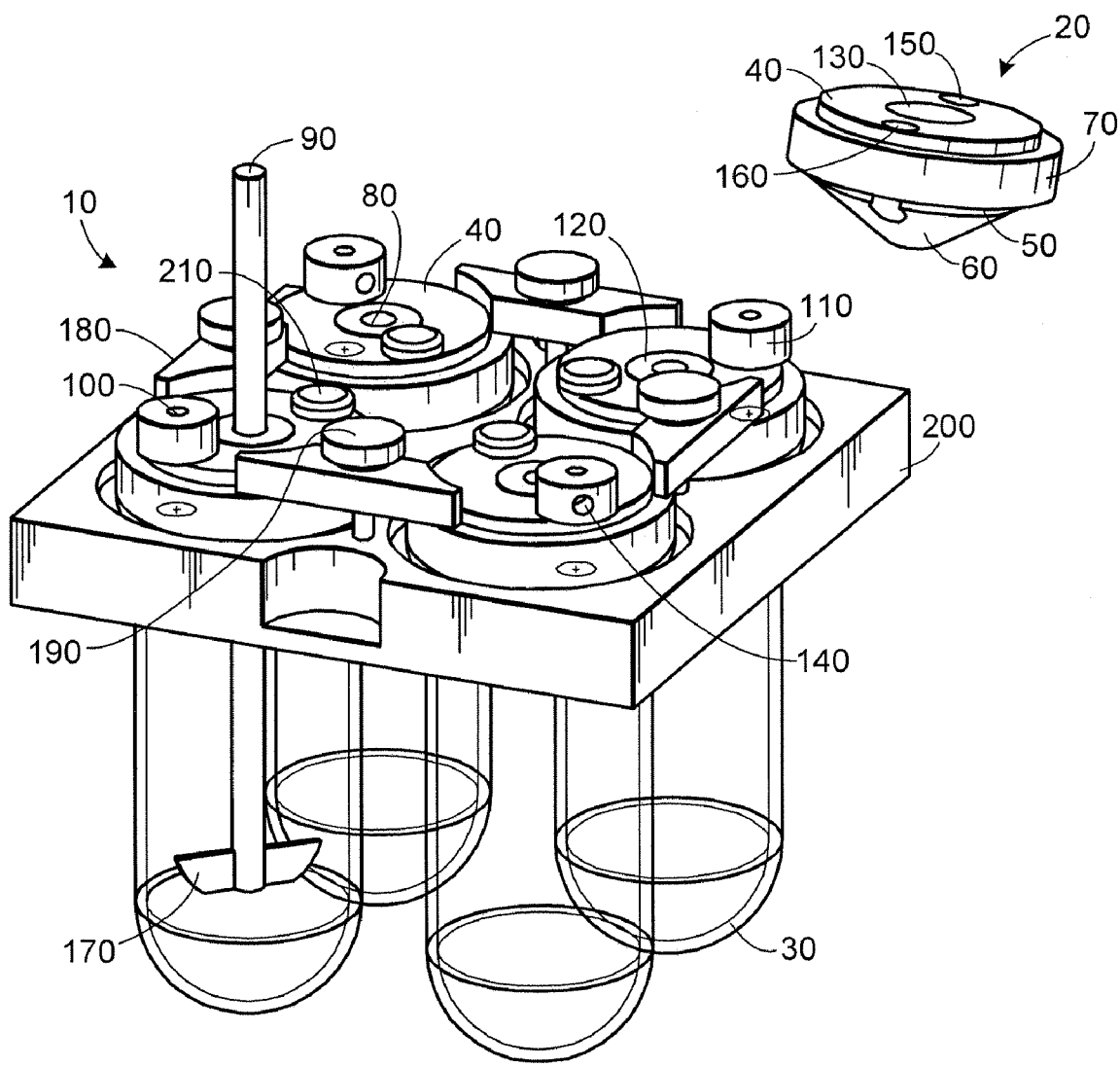
FIG. 7 shows an apparatus that can be used in methods of the invention, one designed to inhibit fluid loss due to evaporation from a fluid dissolution vessel. This specific embodiment of the apparatus (10) comprises a cap (20) for engaging a vessel (30). The central diagram shows a group of four caps operative engaged with vessels and various interactive elements of the apparatus. The diagram at the upper right shows the cap not engaged with a vessel and/or various interactive elements of the apparatus. In the embodiment of the invention shown in this figure, the cap has a first external side (40) and a second internal side (50) that is exposed to a fluid contained in the vessel. The second side (50) comprises a conical member (60) that is designed to direct a condensate that has condensed from the fluid in the vessel onto the second side of the cap back into the fluid. The cap includes a flange (70) disposed between the first external side and the second internal side of the cap. This embodiment shows a central port (80) disposed in the cap adapted to receive a rotatable rod (90), where the material of the central port (typically Teflon) and the material of the rotatable rod are in close contact so as to create a seal that inhibits escape of a material contained within the vessel into the external environment. The rotatable rod in this embodiment includes a fluid agitation member (170) at the distal end of the rod that agitates fluid within the vessel. In this embodiment, the central port (80) is disposed in a central washer (120) that is further disposed within a central washer port (130) on the cap. This embodiment shows a sample port (100) disposed in the cap to allow a user to obtain a sample of the solution from the vessel (or to introduce a composition into the vessel) via a cannula (not shown). In this embodiment, the sample port (100) is disposed in a sample port washer (110) that is further disposed in a sample washer port (160). The sample port washer (110) further includes a cannula securing port (140) that receives a tightening screw member (not shown) that can be used to secure a cannula inserted into the sample port (100) at a desired position. This embodiment further shows a temperature member port (150) adapted to allow a user to introduce a temperature member that contacts and monitors the temperature of the solution within the vessel. The temperature member port (150) is adapted to receive a temperature port cap (210) that can cover the temperature port to inhibit escape of a material within the vessel into the external environment. All of the interacting components in this embodiment of the cap (20) are constructed to closely fit together so as to create seals that inhibits escape of a material within the vessel into the external environment. In addition, a sealing member (not shown) that contacts the vessel (30) that contains the fluid can also be disposed on the cap (20) so as to create a seal with the vessel that inhibits escape of a material within the vessel into the external environment when the cap is operatively engaged with the vessel. The embodiment of the apparatus in this figure further shows a clamp (180) that secures the cap to the vessel via a clamp screw member (190) as well as a rack (200) constructed to hold a plurality of vessels.

FIG. 7 shows a typical embodiment of an apparatus of the invention, one designed to prevent loss due to evaporation from a fluid dissolution vessel. This specific embodiment of the apparatus (10) comprises a cap (20) for engaging a vessel (30). The central diagram shows a group of four caps operative engaged with vessels and various interactive elements of the apparatus. The diagram at the upper right shows the cap not engaged with a vessel and/or various interactive elements of the apparatus. In the embodiment of the invention shown in this figure, the cap has a first external side (40) and a second internal side (50) that is exposed to a fluid contained in the vessel. The second side (50) comprises a conical member (60) that designed to direct a condensate (i.e. liquid formed by the condensation of a vapor or gas) that has condensed from the fluid in the vessel onto the second side of the cap back into the fluid. The cap includes a flange (70) disposed between the first external side and the second internal side of the cap. This embodiment shows a central port (80) disposed in the cap adapted to receive a rotatable rod (90), where the material of the central port (typically Teflon) and the material of the rotatable rod are in close contact so as to create a seal that inhibits escape of a material contained within the vessel into the external environment.

Figure 6:
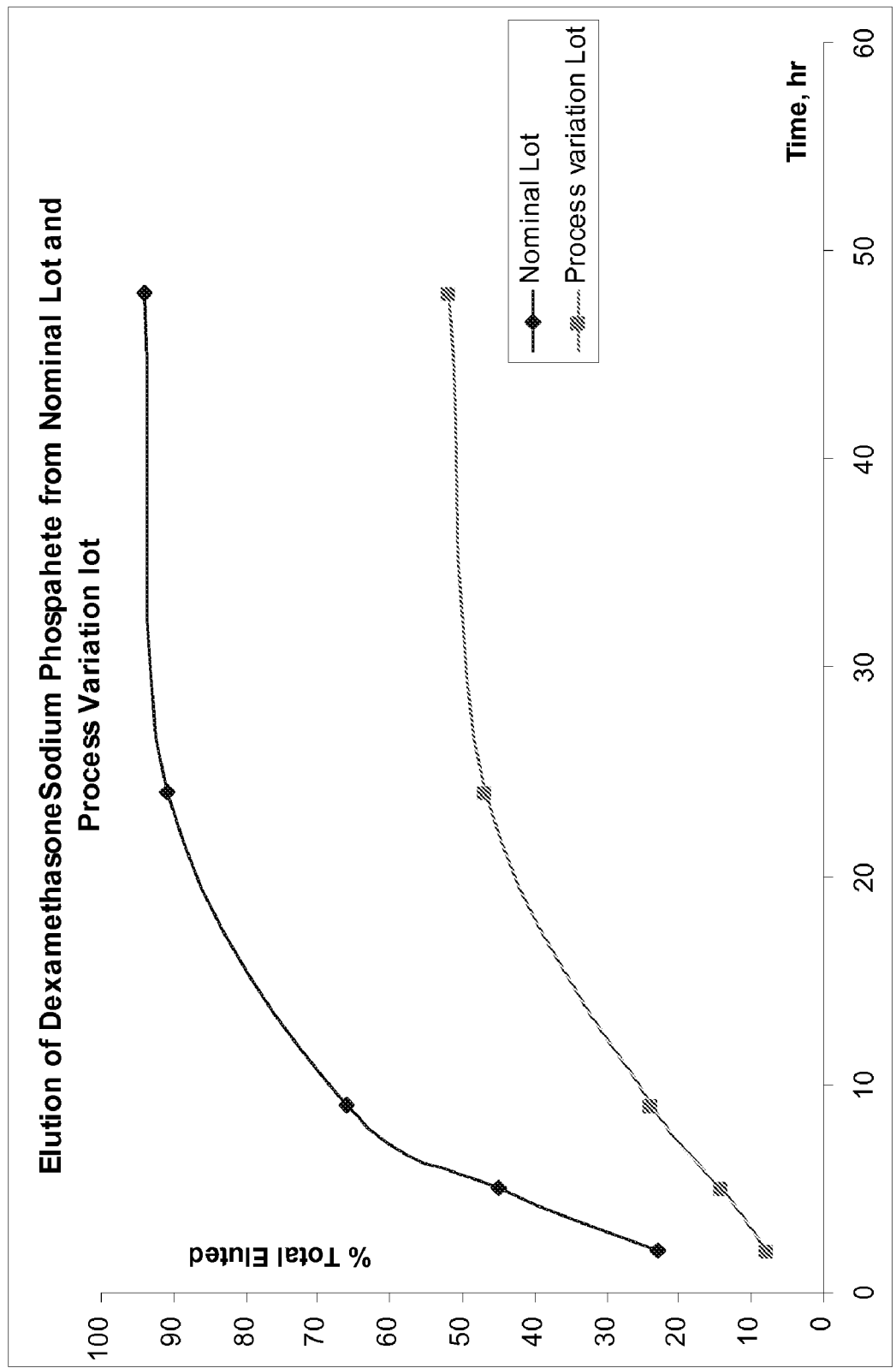
FIG. 6 shows the impact of process changes on elution profile of dexamethasone sodium phosphate from different lots of drug eluting devices. In these elution discrimination studies, the conditions comprised 30% iPA+0.3% DIPA in Phosphate Buffer, pH 8.0 at 45° C.

The rotatable rod in the embodiment of the invention shown in FIG. 6 includes a fluid agitation member (170) at the distal end of the rod that agitates fluid within the vessel. In this embodiment, the central port (80) is disposed in a central washer (120) that is further disposed within a central washer port (130) on the cap. This embodiment shows a sample port (100) disposed in the cap to allow a user to obtain a sample of the solution from the vessel (or to introduce a composition into the vessel) via a cannula (not shown). In this embodiment, the sample port (100) is disposed in a sample port washer (110) that is further disposed in a sample washer port (160). The sample port washer (110) further includes a cannula securing port (140) that receives a tightening screw member (not shown) that can be used to secure a cannula inserted into the sample port (100) at a desired position. This embodiment further shows a temperature member port (150) adapted to allow a user to introduce a temperature member that contacts and monitors the temperature of the solution within the vessel. The temperature member port (150) is adapted to receive a temperature port cap (210) that can cover the temperature port to prevent escape of a material within the vessel into the external environment. A sealing member (not shown) that contacts the vessel (30) that contains the fluid is typically disposed on the cap (20) so as to create a seal with the vessel that inhibits escape of a material within the vessel into the external environment when the cap is operatively engaged with the vessel. In addition, all of the interacting components in this embodiment are constructed to fit together so as to create seals that inhibit escape of a material within the vessel into the external environment so that the apparatus inhibits fluid loss from the vessel due to evaporation. This embodiment further shows a clamp (180) that secures the cap to the vessel via a clamp screw member (190) as well as a rack (200) constructed to hold a plurality of vessels.

In some embodiments of the invention, the apparatus is described as having interacting components constructed to fit together so as to create seals that prevent escape of a material within the vessel into the external environment so that the apparatus inhibits fluid loss from the vessel due to evaporation. In describing a device that "prevents escape of a material contained within the vessel into the external environment", this disclosure is intended for those of skill in this art who understand that a seal that allows the escape of one molecule (or a small number of molecules) within a vessel still prevents or essentially prevents the escape of a material contained within the vessel into the external environment. Further guidelines are provided in this regard to allow one of skill in the art to understand that prevents or essentially prevents escape of a material contained within the vessel into the external environment pertains to. These guidelines include an evaporation loss prevention cover apparatus that allows no more than 10%, preferably no more than 5%, 4%, 3% or 2% and more preferably no more than 1% of the fluid volume to escape from the vessel over a period of 3, 4 or 5, (and optionally 7) days at 25, 37 or 45 degrees centigrade.

As noted above, a typical embodiment is an apparatus for covering a vessel that contains a fluid, the apparatus comprising a cap for engaging the vessel (e.g. a circular cap), the cap having a first external side and a second internal side that is exposed to a fluid contained in the vessel, wherein the second side is cone shaped and/or comprises a conical member that facilitates deposition of a condensate from the fluid back into the fluid. Typically, a flange is disposed between the first external side and the second internal side of the cap. In some embodiments of the invention, the flange engages an edge of the vessel so as to facilitate positioning of the apparatus in an operable orientation.

In certain embodiments of the invention, the cap includes a central port disposed in the cap adapted to receive a rotatable rod that is used to stir a solution within the vessel. Optionally, the central port is disposed in a central washer that is further disposed within a central washer port on the cap. Typically, the central port comprises a teflon material (i.e. a low friction polytetrafluoroethylene polymer) disposed on a portion of the port that contacts the rotatable rod; and the portion of the central port that contacts the rotatable rod creates a seal with the rotatable rod that inhibits escape of a material contained within the vessel into the external environment. Some embodiments of the invention include an apparatus kit that includes additional elements for practicing methods of the invention such as a rotatable rod that can be disposed in the central port, wherein the rotatable rod is disposable through the central port at the portion of the conical member closest to the fluid so as to enter the portion of the vessel that contains the fluid so that the central rod acts as a fluid conduit for the condensate from the second side of the cap back into the fluid contained within the vessel. Typically, the rotatable rod includes a fluid agitation member at the distal end of the rod that agitates fluid within the vessel.

In typical embodiments of the invention, the apparatus includes a sample port disposed in the cap that is adapted to allow a user to obtain a sample of the solution from within the vessel or to introduce a composition into the vessel. Optionally, the sample port is disposed in a sample port washer that is further disposed within a sample washer port on the cap (e.g. as shown in FIG. 7). In one embodiment of the invention, the sample port washer is disposed on the cap to guide and support a cannula that contacts the solution within the vessel. Typically, portions of the sample port washer that contact the cannula and the portions of the sample port washer that contacts the sample washer port create seals that inhibits escape of a material contained within the vessel into the external environment.

In certain embodiments of the invention, a portion of the apparatus that contacts fluid in the vessel (e.g. fluid condensate) is comprised of a material that is resistant to degradation by a solution comprising: 0.03 to 0.05M potassium phosphate buffer at pH range of pH 6 to pH 8; 20-40% isopropyl alcohol; 0.5-6% benzyl alcohol; and 0.2-1% diisopropylamine. In other embodiments of the invention, a portion of the apparatus that contacts fluid in the vessel (e.g. fluid condensate) is comprised of a material that is resistant to degradation by a solution comprising: 0.03 to 0.05M potassium phosphate buffer at pH range of pH 6 to pH 8; 1-12% limonene; 0.3-9% sodium dodecyl sulfate and 0.5-15% lower alkanol. In some embodiments of the invention this portion is made of Delrin. Similarly, in some embodiments of the invention, the O-ring is made of Viton.

Typically, the components of the apparatus (e.g. the washers and washer ports) are designed to fit together so as to create seals that prevent escape of a material within the vessel into the external environment so that the apparatus inhibits fluid loss from the vessel due to evaporation. Moreover, all portions of the apparatus that allow access to the fluid within the vessel (e.g. the central and sample ports) can be adapted to receive a cap member that covers the port so as to inhibit escape of a material within the vessel into the external environment. In addition, in typical embodiments of the invention, the cap is of unitary construction, meaning that its material is made from a single cast of material and has no seams or joints that provide avenues for fluid loss. In an exemplary embodiment of the invention, the apparatus reduces fluid loss due to evaporation to less than 5%, 4%, 3%, 2% or 1% of the fluid contained within the vessel over 7 days at 37 degrees centigrade. In another exemplary embodiment of the invention, the apparatus reduces fluid loss due to evaporation to less than 5%, 4%, 3%, 2% or 1% of the fluid contained within the vessel over 15 days at 37 degrees centigrade.

The methods and apparatuses disclosed herein can be adapted for use in a wide variety of procedures known in the art. All patent and literature references (e.g. Shah et al., International Journal of Pharmaceutics 125 (1995) 99-106; AAPS PharmSci 2002; 4 (2) article 7; AAPS PharmSci 2004; 6 (1) Article 11; Guidance for Industry, Extended Release Oral Dosage Forms: Development, Evaluation, and Application of In Vitro/In Vivo Correlations, U.S. Department of Health and Human Services Food and Drug Administration Center for Drug Evaluation and Research (CDER), September 1997, BP 2; Palamakula et al., Preparation and In Vitro Characterization of Self-Nanoemulsified Drug Delivery Systems of Coenzyme Q10 Using Chiral Essential Oil Components, Pharmaceutical Technology OCTOBER 2004; Lawrence et al., Advanced Drug Delivery Reviews 45 (2000) 89-121 and U.S. Patent and Patent Application Nos. 6,063,314; 4,819,662; 5,464,650; 5,609,629; 20040037886; and 20030208236) are incorporated by reference herein.

Embodiments of the invention include kits comprising a first container, a label on said container, and a composition contained within said container. Such kits include elution media components in one or more containers having a label, the label on said container, or a package insert included in said container indicates that the composition can be used to elute a composition form a matrix. Optionally the kit includes a premixed, ready to use elution media. Optionally the kit includes additional elements such as an apparatus for using the media, an embodiment of which is shown in FIG. 7. Other embodiments of the invention include a kit containing an apparatus for using the media, an embodiment of which is shown in FIG. 7, in the absence of elution media components.

EXAMPLES

Example 1

Illustrative Methods and Materials Used to Practice Embodiments of the Invention Elution Procedure Typical Dissolution System Setup The following provides illustrative methods and materials useful with embodiments of the invention. It is to be understood, however, that these illustrative examples, while indicating some embodiments of the present invention are given by way of illustration and not limitation. Many changes and modifications within the scope of the present invention may be made without departing from the spirit thereof, and the invention includes all such modifications.

Illustrative elution parameters are shown in Table 1.

TABLE 1

Typical Elution Parameters

| Parameter | Specification |
| --- | --- |
| Illustrative Apparatus | USP Apparatus 2 with mini vessels, mini paddles, covered by low evaporation loss covers and/or USP Apparatus 1 with mini vessels, mini baskets, covered by low evaporation loss covers Other USP dissolution apparatus or modifications therein can be used. |
| Illustrative Media Information | 0.05M phosphate buffer having at pH 8; 30% isopropanol; and <1% diisopropyl amine, or <1% benzyl alcohol |
| Illustrative Media Volume | 75 ml |
| Illustrative Media Temperature: | 45.0 ± 0.5° C. |
| Illustrative Media withdrawn/replaced | 1 ml |
| Illustrative Shaft Speed | 100 rpm |
| Illustrative Evaporation Control | Special low evaporation loss covers |
| Typical Time Points* | 6 hr, 12 hr, Day 1, Day 2, Day 3, Day 4, Day 6, Day 8, Day 10, Day 12 |

Method Development

The steps in method development can include adaptations of methods and materials known in the art, for example USP General Chapter <1092>, *In-Process Revision*, "The Dissolution Procedure: Development and Validation", Pharmacopeial Forum, 2005, 31 (5), p. 1463; Burgess et al., "Assuring Quality and Performance of Sustained and Controlled Release Parenterals: Workshop Report", AAPS PharmSci, 2002, 4(2), article 7; and Burgess et al., "Assuring Quality and Performance of Sustained and Controlled Release Parenterals: EUFEPS Workshop Report", AAPS PharmSci, 2004, 6(1), article 11.

A first step can be to determine the solubility of the product using standard aqueous elution media, several of which are listed in the USP (see, e.g. USP General Chapter <724>, "Drug Release"), literature (see, e.g. Noory et. al., (Food and Drug Administration—CDER), "Steps for Development of a Dissolution Test for Sparingly Water-soluble Drug Products", Dissolution Technologies, 2000, 7(1), Article 3) and the US FDA website (see, e.g. FDA website link for elution/dissolution medias using search terms: "accessdata.fda.gov/scripts/cder/dissolution/"). The initial run can allow evaluation of the effect of pH on the product. If the product exhibits poor dissolution, then the need for further agents such as surfactants (below the critical micelle concentration forming emulsions) can be evaluated.

Dexamethasone sodium phosphate is a steroid, freely soluble in water. Dexamethasone sodium phosphate is typically distributed in the polymer matrix of a implantable medical device such as a cardiac lead as a dispersion. The drug generally diffuses from the matrix into the fluidic system where the lead is placed. In typical embodiments of the invention, it is important to use a dissolution medium that exhibits good thermodynamic compatibility with the polymer (see, e.g. Peppas et al., "Modeling of Drug Diffusion through Swellable Polymeric Systems", Journal of Membrane Science, 1980, 7, p. 241-253; and Paul, D. R., "Controlled Release Polymeric Formulations", ACS Symposium Series, volume 33, ACS, Washington, 1976.

A literature survey showed that the elution of dexamethasone acetate-eluting cardiac pacing electrodes is less than 19% in 24 days if PBS (without additives) is used (see, e.g. Casas-Bejar et. al., "Medical Electrical Leads and in-dwelling Catheters with enhanced Biocompatibility and Biostability", United States Patent Publication, Publication # US 20020138123 A1, Application Number 998536, Sep. 26, 2002) (PBS=Phosphate Buffered Saline). Another study conducted by Guidant Corporation, showed elution at about 10% in 30 days (see, e.g. Heil, R (Guidant Corporation), "In Vivo Comparison of Dexamethasone-eluting cardiac pacing electrode technologies with different release rates", Proceed. Int'l. Symp. Control. Rel. Bioact. Mater., 2000, 27, p. 471). The percent elution was less than 7% in 10 days from the CRD leads when PBS (pH 5) without any additives was used. The information indicates that though the drug may be soluble in the buffered media at low concentrations (see sink condition evaluation below), the drug dissolution will be controlled by diffusion from the polymer.

Preparation of Device for Elution Studies

The drug eluting portion of samples can be cut separately from the device and used for the purpose of testing. The CRD section can be cut from the device such that the length of the section can be approximately 1-2 cm.

Choice of Elution Parameters

To evaluate buffers with different pH, Dexamethasone sodium phosphate can be dissolved in an elution media (e.g. one of the different embodiments of the invention disclosed herein). The stability of Dexamethasone sodium phosphate with respect to pH follows this order: pH 4>pH 7.5>pH 9. This concentration was about 10 times the concentration that might be observed if the drug from the typical device was completely eluted in about 75 mL of media.

A next step can involve attempting to increase the elution by adding different types of additives, capable of forming macro-emulsions, to the media. This can be in concurrence with the USP, US FDA and industry guidelines for performing elution on a sparingly soluble drug substance (see, e.g. USP General Chapter <1092>, "The Dissolution Procedure: Development and Validation", Pharmacopeial Forum, 2005, 31 (5), p. 1463; FDA Guidance for Industry (CDER), "Extended Release Oral Dosage Forms: Development, Evaluation and Application of In Vitro/In Vivo Correlations", September 1997; FDA Guidance for Industry (CDER), "Immediate Release Solid Oral Dosage Forms Scale-Up and Postapproval Changes: Chemistry, Manufacturing, and Controls, In Vitro Dissolution Testing, and In Vivo Bioequivalence Documentation", November 1995; 4. Burgess et al. "Assuring Quality and Performance of Sustained and Controlled Release Parenterals: Workshop Report", AAPS PharmSci, 2002, 4(2), article 7; Burgess et al., "Assuring Quality and Performance of Sustained and Controlled Release Parenterals: EUFEPS Workshop Report", AAPS PharmSci, 2004, 6(1), article 11, respectively). The suitability of different classes of surfactants, namely, anionic (e.g. sodium dodecyl sulfate), cationic (e.g. Cetyl trimethyl ammonium bromide—CTAB) and non-ionic (e.g. Solutol HS 15-poly-oxyethylene esters of 12-hydroxystearic acid, Tween 80) as an additive to the elution media can be evaluated.

Choice of Apparatus

The apparatus chosen for this method can be that shown for example in FIG. 7 or one known in the art such as USP Apparatus 2 (Paddles). Due to the low content of the drug in the device, mini vessels with mini paddles can be chosen for the method. The apparatus can be set at 100 rpm. A media volume of 75 mL is appropriate for the analytical methods detection capability and meets typical the sink conditions. The media can be maintained at 32-45° C.±0.5° C. The sample pull volume can be 1 mL at each time point with media compensation, in line with elution guidelines.

Choice of Analytical Method of Quantification of Dexamethasone Sodium Phosphate

The initial choice of analytical method can be UV-Vis. However, due to the low concentration of drug present in the material, HPLC with UV detection can also be used The mobile phase preparation and choice of the column can be instructed in the agent (e.g. Dexamethasone sodium phosphate) monograph. The chromatographic column (USP L11) used can be an Phenomenex Luna Hexyl-Phenyl 4.6 mm×250 mm, 5 µm. A gradient can be used with 1 mL/min flow rate. The run time can be about 35 minutes. The UV detection wavelength can be 254 nm, where the method can be found to be specific for quantification of Dexamethasone Sodium phosphate in the elution medium. The injection volume for standard and samples can be 100 µL.

Sampling Time Points and Elution Data

The elution of Dexamethasone sodium phosphate from a CRD can be examined using embodiments of the invention disclosed herein. FIGS. 1-6 show typical plots of elution of dexamethasone sodium phosphate from CRDs. The elution pattern for CRD were similar to the profile of a non-disintegrating product (see, e.g. Hanson, R., Gray, V., Handbook of Dissolution Testing, Page. 22, $3^{rd}$ Edition, Dissolution Technologies, Inc, Hockessin, Del.). This profile was generally obtained where the dissolution rate was determined by the process of diffusion and dissolution.

As shown in FIGS. 1-6, different nominal lots of the typical CRD can be analyzed using the embodiments of the invention.

Elution Discrimination Studies

As shown in FIGS. 1-6, the discriminating nature of the elution method can be used to study differing lots of the same device. One lot can manufactured using the nominal process and other lots can be manufactured with different process variations. The elution method can be used to discriminate between the nominal and process variation lots.

All patent and literature references cited in the present specification are hereby incorporated by reference in their entirety.

The invention claimed is:

1. A method of observing the elution of a compound from a matrix into an aqueous media, the method comprising exposing a matrix comprising the compound to a media, wherein the media comprises:
   20-40% of a lower alkanol; and
   0.2-6.0% of a matrix swelling agent; wherein the matrix swelling agent comprises at least:
   0.2-1.0% diisopropyl amine;
   0.2-1.0% dipropylamine;
   0.2-1.0% tetramethylenediamine;
   0.2-1.0% tributylamine; or
   0.5-6.0% benzyl alcohol;
   and
   assaying the media for the presence of the compound so as to observe the elution of the compound from the matrix into the media.

2. The method of claim 1, wherein the media comprises:
   0.03 to 0.05M phosphate buffer having a pH range of pH 6 to pH 8.

3. The method of claim 1, wherein the media comprises:
   0.05M phosphate buffer having pH 8;
   30% isopropanol; and
   <1% diisopropyl amine, or <1% benzyl alcohol.

4. The method of claim 1, further comprising performing the method on a plurality of matrices made by a process designed to produce a plurality of matrices that elute the compound at the same rate and comparing the elution rates of two or more of plurality of matrices to determine if the two or more matrices have the same or different elution rates.

5. The method of claim 1, wherein the media is assayed for the presence of the compound using high performance liquid chromatography (HPLC).

6. The method of claim 5, wherein the matrix comprising the compound is a polymer matrix having the compound blended therein.

7. The method of claim 6, wherein the matrix comprises a biomedical grade silicone polymer or a biomedical grade polyurethane polymer.

8. The method of claim 1, wherein the compound comprises a steroid, an anti-coagulant an antibiotic, or an anti-inflammatory agent.

9. The method of claim 8, wherein the compound is dexamethasone sodium phosphate.

10. The method of claim 1, wherein the matrix comprising the compound is implantable in vivo.

11. The method of claim 1, further comprising observing elution at a media temperature of between 25 and 45 degrees centigrade.

12. The method of claim 1 further comprising agitating the media with a stirring device.

13. The method of claim 1, wherein the volume of the media is between 50 and 150 milliliters.

14. The method of claim 1, further comprising using a media in the method that is selected for its ability to elute at least 50% of dexamethasone sodium phosphate impregnated within a polymeric silicone in 72 hours at 45 degrees centigrade.

15. A system for observing the elution of a compound from a polymeric matrix into an aqueous media, the system comprising:
 a) a composition of matter comprising an aqueous solution of:
 20-40% of a lower alkanol; and
 one or more matrix swelling agents comprising:
 0.2-1.0% diisopropyl amine;
 0.2-1.0% dipropylamine;
 0.2-1.0% tetramethylenediamine;
 0.2-1.0% tributylamine; or
 0.5-6.0% benzyl alcohol; and
 b) a polymeric matrix impregnated with an elutable agent comprising a steroid, an anti-coagulant, an antibiotic, or an anti-inflammatory agent.

16. The composition of matter of claim 15, wherein the lower alkanol is isopropanol.

17. The composition of matter of claim 15, wherein the media comprises:
 0.03 to 0.05M potassium phosphate buffer having a pH range of pH 6 to pH 8;
 30% isopropanol; and
 <1% diisopropyl amine, or <1% benzyl alcohol.

18. The system of claim 15, wherein the matrix is adapted for use as part of a drug eluting medical device.

* * * * *